United States Patent
D'Alesio

(10) Patent No.: US 10,850,163 B2
(45) Date of Patent: Dec. 1, 2020

(54) MOVABLE PLATFORM FOR PHYSICAL EXERCISE

(71) Applicant: REAXING S.R.L., Milan (IT)

(72) Inventor: Gionata D'Alesio, Ascoli Piceno (IT)

(73) Assignee: REAXING S.R.L., Milan (IT)

( * ) Notice: Subject to any disclaimer, the term of this patent is extended or adjusted under 35 U.S.C. 154(b) by 0 days.

(21) Appl. No.: 16/072,700

(22) PCT Filed: Jan. 25, 2017

(86) PCT No.: PCT/IB2017/050386
§ 371 (c)(1),
(2) Date: Jul. 25, 2018

(87) PCT Pub. No.: WO2017/130112
PCT Pub. Date: Aug. 3, 2017

(65) Prior Publication Data
US 2019/0030399 A1    Jan. 31, 2019

(30) Foreign Application Priority Data

Jan. 26, 2016   (IT) .................... 102016000007697

(51) Int. Cl.
*A63B 26/00* (2006.01)
*A63B 22/18* (2006.01)
(Continued)

(52) U.S. Cl.
CPC .............. *A63B 26/003* (2013.01); *A61B 5/11* (2013.01); *A61H 1/0266* (2013.01);
(Continued)

(58) Field of Classification Search
CPC ................. A63B 26/003; A63B 22/16; A63B 22/02–0292; A63B 24/0087
See application file for complete search history.

(56) References Cited

U.S. PATENT DOCUMENTS 5,902,214 A    5/1999 Makikawa et al.
6,878,102 B1   4/2005 Commisso
(Continued)

FOREIGN PATENT DOCUMENTS

CN    101006958 A     8/2007
WO    2013/093787 A1  6/2013
WO    2014/085732 A1  6/2014

OTHER PUBLICATIONS

Shumway-Cook, "Assessing the Influence of Sensory Interaction on Balance", Physical Therapy, 1986, pp. 1548-1550, vol. 66, No. 10.
(Continued)

*Primary Examiner* — Jennifer Robertson
(74) *Attorney, Agent, or Firm* — Nixon & Vanderhye

(57) ABSTRACT

Disclosed is a movable platform for physical exercise including: a fixed base; at least one board having an upper surface to accommodate at least one person who must perform a physical exercise or also sporting equipment, the board being connected to the base with the possibility of rotating about at least one axis and/or of moving at least along one direction; an actuator, interposed between the base and the board, configured to impart to the board at least a rotation about the at least one axis, at least a movement at least along the direction, or combinations of these movements; a control unit, operatively connected to the actuator, configured to control activation or deactivation of the actuator to rotate and/or move the board between a reference position and perturbed positions, the control unit generating a sequence of motor interferences that influence the balance of the person performing the exercise.

20 Claims, 6 Drawing Sheets

(51) Int. Cl.
  *A63B 24/00* (2006.01)
  *A63B 69/00* (2006.01)
  *A61H 1/02* (2006.01)
  *A63B 21/005* (2006.01)
  *A63B 21/00* (2006.01)
  *A63B 23/08* (2006.01)
  *A61B 5/11* (2006.01)
  *A63B 22/14* (2006.01)
  *A63B 22/16* (2006.01)
  *A61H 1/00* (2006.01)
  *A63B 22/00* (2006.01)
  *A63B 71/06* (2006.01)
  *A63B 71/00* (2006.01)
  *A61B 5/024* (2006.01)

(52) U.S. Cl.
  CPC .... *A63B 21/0058* (2013.01); *A63B 21/00178* (2013.01); *A63B 21/00181* (2013.01); *A63B 21/4015* (2015.10); *A63B 21/4034* (2015.10); *A63B 22/14* (2013.01); *A63B 22/16* (2013.01); *A63B 22/18* (2013.01); *A63B 23/08* (2013.01); *A63B 24/0062* (2013.01); *A63B 24/0087* (2013.01); *A63B 69/0064* (2013.01); *A61B 5/024* (2013.01); *A61H 1/005* (2013.01); *A61H 2201/018* (2013.01); *A61H 2201/0176* (2013.01); *A61H 2201/1215* (2013.01); *A61H 2201/1246* (2013.01); *A61H 2201/1481* (2013.01); *A61H 2201/164* (2013.01); *A61H 2201/1642* (2013.01); *A61H 2201/1659* (2013.01); *A61H 2201/1664* (2013.01); *A61H 2201/1676* (2013.01); *A61H 2201/5002* (2013.01); *A61H 2201/5061* (2013.01); *A61H 2201/5064* (2013.01); *A61H 2201/5092* (2013.01); *A63B 69/0057* (2013.01); *A63B 71/0622* (2013.01); *A63B 2022/0092* (2013.01); *A63B 2022/0094* (2013.01); *A63B 2024/009* (2013.01); *A63B 2024/0068* (2013.01); *A63B 2024/0093* (2013.01); *A63B 2024/0096* (2013.01); *A63B 2071/0081* (2013.01); *A63B 2071/0683* (2013.01); *A63B 2208/0204* (2013.01); *A63B 2220/16* (2013.01); *A63B 2220/24* (2013.01); *A63B 2220/52* (2013.01); *A63B 2220/805* (2013.01)

(56) References Cited

U.S. PATENT DOCUMENTS

| | | | |
|---|---|---|---|
| 9,730,852 | B2 | 8/2017 | Malosio et al. |
| 2011/0177917 | A1 | 7/2011 | Patel |
| 2011/0256983 | A1 | 10/2011 | Malack et al. |
| 2013/0237395 | A1* | 9/2013 | Hjelt ............... A63B 22/18 |
| | | | 482/146 |
| 2015/0238816 | A1* | 8/2015 | Naderer ........... A63B 22/16 |
| | | | 482/4 |
| 2015/0328497 | A1 | 11/2015 | Doucot et al. |
| 2016/0059068 | A1* | 3/2016 | Olson ........... A63B 22/0023 |
| | | | 482/5 |

OTHER PUBLICATIONS

International Search Report and Written Opinion, dated May 30, 2017, from corresponding PCT application No. PCT/IB2017/050386.

* cited by examiner

MOVABLE PLATFORM FOR PHYSICAL EXERCISE

BACKGROUND OF THE INVENTION

Field of the Invention

The present invention relates to a movable platform for physical exercise. More in detail, the invention relates to a platform with a supporting surface to support a person and/or sporting equipment, provided with means adapted to move said supporting surface during the performance of an exercise.

The invention falls within the sector of sporting equipment suitable to stimulate the reaction of the human body to so-called motor interferences, i.e. external stimuli that, during the performance of a movement, can generate a variation of the balance of a person.

Usually, training of the muscles of the body involves the performance of free body exercises or exercises with equipment (movable equipment or stationary machines).

During the performance of these exercises, the person or the machine rests on a stable support, such as a floor, a fixed platform or the like.

According to this training method, the person contracts his/her muscles voluntarily to perform a given movement characteristic of the exercise that he/she is performing.

In practice, during the performance of an exercise, any variation of position, acceleration or speed of a part of the body, just as the force exerted by given muscles, is known or in any case predictable by the person performing the exercise.

However, both in the practice of some sporting activities and in normal daily actions, our body is often subjected to external stimuli, predictable or unpredictable, that can interfere with a movement that is being performed or with a condition of stable balance.

For example, in a sporting activity, contact with an opponent or an unexpected change in direction can cause an imbalance that the athlete must compensate as rapidly as possible.

In other cases, these interferences can be generated, especially when running, by incorrect positioning of the foot on the ground, due to a coordination error of the athlete or to an unexpected variation of the ground underfoot.

An event of this kind can also occur during daily activities, such as walking, climbing stairs or in other more precarious conditions of balance.

Examples of motor interferences are also represented, for example, by losing one's grip on and dropping an object and trying to catch it.

In general, the greater the rapidity and unexpectedness of the interference that occurs, the more difficulty the body has in reacting correctly to re-establish the condition of movement, or of unperturbed balance.

Description of the Related Art

In this regard, studies by Shumway-Cook A and Woollacott M H, Nasher L M, McIlroy W E and Maki B, Shumway-Cook A and Horak F B (see detailed bibliography), show that this capacity of our body to react can be developed and increased with a training method in which motor interferences are suitable imparted to the person during the performance of physical exercises.

BRIEF SUMMARY OF THE INVENTION

An objective of the present invention is therefore to provide an instrument that allows a person to perform a physical exercise perturbed by unexpected and unknown motor interferences.

The purpose of this instrument is, therefore, that of artificially reproducing motor interferences that a person, and in particular an athlete during the performance of a sporting activity, could be subjected to.

In this context, it is therefore an object of the present invention to propose an apparatus that allows the generation of motor interferences capable of interfering with the balance of a person is performing the exercise and hence to stimulate a reaction thereof.

Another object of the present invention is to propose an apparatus capable of generating motor interferences with parameters variable as a function of information detected during performance of the exercise.

Another object of the invention is to provide an apparatus controllable in real time by a third person, for example a trainer or an instructor.

Yet another object of the present invention is to provide an apparatus that allows a person to perform a plurality of exercises, both free body and with the aid of exercise equipment or machines.

These objects are achieved by a movable platform that comprises a board on which a person who is to perform a physical exercise can be stationed. The person can be supported directly by the board, for example standing, sitting or lying thereon, or indirectly, by means of sporting equipment. Actuator means are configured to rotate or move the board so as to vary the position of the supporting surface that supports the person or the equipment, according to a given sequence of one or more movements. These unexpected movements generate motor interferences for the person performing the exercise, i.e. they compromise, at least in part, balance, stimulating a muscular reaction to find a new condition of balance.

Therefore, the subject matter of the present invention is a movable platform for physical exercise comprising a base, generally fixed, for example resting on the ground, and at least one board. The board is connected to said base so as to rotate about at least one axis and/or to move along at least one direction. Said board can accommodate at least one person who is to perform a physical exercise and optionally sporting equipment. The platform also comprises actuator means configured to rotate the board at least about said axis and/or to move it at least along said direction. A control unit, operatively connected to the actuator means, controls activation or deactivation thereof to impart to the board rotations and/or movements according to a given sequence. This sequence of movements causes a corresponding sequence of motor interferences for the person performing the physical exercise or, in any case, a given movement.

Typically, these motor interferences are not known to the person performing the exercise and, therefore, they can simulate unexpected events that occur normally during sporting activity or daily activities.

By subjecting the person to these unexpected disturbances, during the performance of a physical exercise or of a specific movement, it is possible to stimulate and train the respective reactions of the muscles of the body.

In an aspect of the invention, the movable platform can comprise sensor means operatively connected to the control unit. These sensors are configured to measure one or more parameters concerning the person performing the exercise or the sporting equipment, or both. The control unit is configured to receive the measurement of the aforesaid parameters and to program accordingly, also in real time, the sequence of motor interferences to impart to the person.

The control unit is therefore capable of generating, also in real time, a given sequence of motor interferences as a function of one or more parameters concerning the exercise being performed.

For example, the control unit can determine, in conformity with these parameters, the type of movement to impart to the board (rotation, translation, etc.), the initial moment, the rapidity, the duration or the intensity of this movement.

In a preferred aspect of the invention, said at least one parameter can be selected from quantities such as the position, the speed or the acceleration of at least a part of the body of the person, of the sporting equipment used, or of both.

Another quantity detectable can be a force (for example a weight force), transferred to the board or to a part of the equipment.

Another parameter detectable and usable to modulate the sequence of motor interferences is the fatigue or energy expenditure of the person.

Said sensor means can therefore comprise optical sensors, ultrasonic sensors, load cells, inductive sensors, video cameras, accelerometers, encoders, magnetometers, gyroscopes or heart rate monitors.

These sensors, as a function of their structure, can be applied to the movable platform, on the base or on the board, to the sporting equipment or directly to the body of the person.

In another aspect of the invention, the movable platform can comprise an interface, operatively connected to the control unit, that allows interaction with the person performing the exercise or with another user. Said interface can be configured to allow viewing of information concerning the sequence of motor interferences and, optionally, to program some parameters of said sequence.

Preferably, according to an aspect of the invention, programs corresponding to sequences of motor interferences having given parameters are stored in the control unit.

By means of said interface, a user can manually set the parameters of the sequence of motor interferences or can select one of the programs stored in the control unit.

Moreover, the control unit can be configured to correct the parameters of the sequence of motor interferences being performed as a function of the parameters detected by the sensor means.

According to another aspect of the invention, the movable platform comprises control means, connected to the control unit, configured to impart one or more parameters of the sequence of motor interferences. Said control means are generally usable by a third person who is not performing the exercise and who therefore is not on the board.

Said control means can, for example, comprise one or more accelerometers applicable to the body of said third person, a voice control system managed by said third person or one or more video cameras arranged to film said third person.

In another aspect of the invention, the actuator means are configured to impart to the board rotations and movements with amplitudes, speeds or accelerations such as to generate motor interferences capable of stimulating the reaction of the body.

Values suitable for this object, for a rotation of the board, are those indicated in one or more of the ranges below:
an angle from 3° to 30°;
an angular velocity from 0.05 rad/s to 0.5 rad/s;
an acceleration from 0.01 rad/s$^2$ to 0.1 rad/s$^2$.

For a movement of the board, corresponding suitable values are indicated in one or more of the ranges below:
an amplitude from 5 mm to 250 mm;
a speed from 0.02 m/s to 0.5 m/s;
an acceleration from 0.01 m/s$^2$ to 0.05 m/s$^2$.

The values indicated above are apt to replicate motor interferences suitable to generate an instability or a temporary loss of balance of the person. They are therefore stimuli comparable with those to which a person can be subjected in the performance of a given sporting activity (professional or amateur) or of daily activities.

According to another aspect of the invention, the actuator means to generate the aforesaid motor interferences can comprise electric actuators, hydraulic actuators, pneumatic actuators or electromagnets.

The board can be connected to the aforesaid actuators directly or by means of joints or the like.

In a particular embodiment, the movable platform can be integrated with a treadmill. In this variant the board is provided with a pair of rollers, rotatingly connected to the board and arranged so that the respective rotation axes are parallel to one another and substantially parallel to the upper surface of the board. A belt is wound around said rollers and arranged so as to have at least an upper branch positioned above said upper surface of the board. At least one motor is connected to at least one of said rollers to rotate said belt.

BRIEF DESCRIPTION OF THE DRAWINGS

Further characteristics and advantages of the present invention will become more apparent from the description of an example of a preferred, but not exclusive, embodiment of a movable platform for physical exercise, as illustrated in the accompanying figures, wherein.

DETAILED DESCRIPTION OF THE PREFERRED EMBODIMENTS

Figure 1:
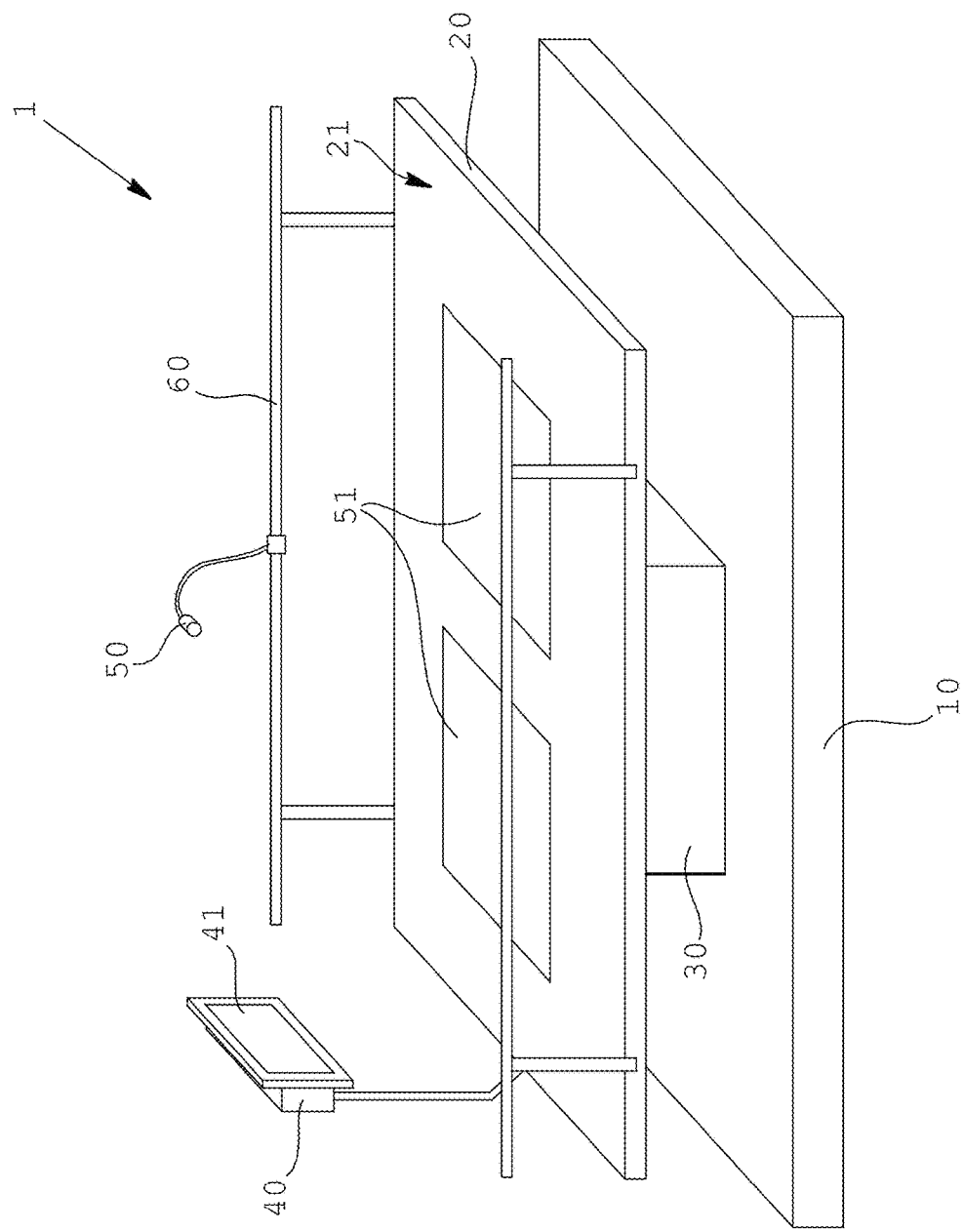
FIG. 1 is a schematic view of the movable platform according to the invention.

With reference to FIG. 1, the numeral 1 indicates as a whole a movable platform according to the invention, represented in a simplified manner.

The platform comprises a base 10. Said base 10 is suitably configured to be positioned on a stable surface, such as a floor. Said base 10 is therefore typically fixed.

Positioned above said base 10, and supported thereby, is at least one board 20.

The board 20 has an upper surface 21, preferably flat and continuous, which defines a supporting surface. Said supporting surface can accommodate at least one person and optionally one or more pieces of exercise equipment used in the performance of an exercise (not illustrated in the figure).

As a function of the extension of said upper surface 21, the person can remain standing on the platform, for example with both feet resting thereon, or lying or in any other position required to perform a physical exercise.

The equipment that can be accommodated on the platform can be either sporting equipment, for fitness or for professional training, or rehabilitation equipment.

Moreover, this equipment can be of fixed type, such as weight lifting machines, multifunction machines, benches, treadmills, typically bulky and heavy, or movable equipment such as barbells, dumbbells, kettlebells, ropes, elastic bands, strips, etc.

These latter can be positioned, removed or replaced directly by the person who wishes to use the platform.

More in general, the board 20 is configured to allow one or more people to perform any type of physical exercise, free body or with the aid of equipment, which involves a limited movement of the person on the supporting surface.

For this purpose, preferably the upper surface 21 of the board 20 has a useful area, in which the exercise can be performed, of at least 1 m². However, this upper surface 21 can have a larger useful area, for example from 2 m² to 6 m², suitable to accommodate at least one person and optionally equipment.

According to a variant of the invention, on the upper surface 21, the board is provided with coupling means (not illustrated in the figure) for connection of exercise equipment.

Said coupling means can, for example, comprise rings, bayonet couplings, magnets or the like. Preferably, said coupling means are embedded under said upper surface 21 and can be covered with covers, so as to be concealed when not in use.

Said coupling means can be used for the connection of equipment such as elastic bands, handles or the like or for fixing equipment such as treadmills, exercise bikes, benches, poles or parallel bars or the like, to the board.

According to the invention, the board 20 is connected to the base 10 so as to be able to rotate and/or move with respect thereto.

As a function of the type of exercise to be performed, or of the type of equipment positioned on the supporting surface of the board, this latter can have a number of degrees of freedom, preferably from one to three.

In a first example, the board 20 can rotate about an axis. Preferably, said rotation axis lies on a plane X-Y substantially horizontal or substantially parallel to the surface on which the base 10 rests.

In another example, the board 20 can move along a direction Z, preferably substantially perpendicular to the plane X-Y or to the surface on which the base 10 rests.

Differently, the board 20 can rotate or move in space along more than one direction transverse to one another. For example, the board 20 can have at least three degrees of freedom, of which two degrees of freedom are rotations about axes that lie on the plane X-Y and one degree of freedom is a translation along the axis Z.

The board according to the invention can have different plan shapes. For example, it can be square, rectangular, circular or a generic polygonal, curved or mixed shape.

However, a regular polygonal shape is preferable as it allows references to be established, with respect to which the movements of the board can be compared.

These references can, for example, comprise the position of the sides of the board with respect to an absolute reference (front side, rear side, right side, left side, etc.) or the position of reference rotation axes (longitudinal axis, transverse axis, etc.).

The rotations and/or the movements are imparted to the board 20 by actuator means 30, schematized in FIG. 1.

According to some variants of the invention, illustrated more in detail below, the actuator means 30 can be electric actuators, for example rotary or linear motors, hydraulic actuators, pneumatic actuators, for example cylinders or air springs, or electromagnets.

Control of said actuator means 30 is entrusted to a control unit, indicated with 40 in the accompanying figures.

More in detail, said control unit 40 is operatively connected to the actuator means 30 and is configured to activate and deactivate these latter to generate a sequence of motor interferences.

In particular, the control unit 40 establishes the moment in which an actuator must be activated or deactivated, the rapidity of its movement and its extension (angular or linear).

The coordinated movement of one or more actuators determines the movement in space of the board 20 from a reference position, for example in which the supporting surface is substantially horizontal, to a perturbed position.

Therefore, the term sequence of motor interferences indicates a sequence of one or more variations of position of the board with respect to the aforesaid reference position. During the performance of a sequence of motor interferences, the board 20 can return several times to the reference position or can move between different perturbed positions.

As already mentioned, the object of the invention is to use the aforesaid motor interferences, generated through the rotations or the movements of the board 20, to stimulate the person during the performance of an exercise, or more in general of a predetermined movement, or in a condition of balance.

Rotations or movements of the board that are too brief or too slow might not be sufficient to generate motor interferences, i.e. suitable to stimulate the reaction of the body.

On the contrary, rotations or movements that are too fast or too broad could be dangerous for some subjects or during the performance of given exercises.

For this reason, the control unit 40 is preferably of programmable type. In particular, the control unit is configured to allow setting of given parameters concerning the sequence of motor interferences to be generated.

Typically, these parameters comprise one or more of the following quantities referred to a rotation and/or to a movement of the board 20:
the direction or the sense;
the amplitude;
the speed;
the acceleration.

According to tests carried out by the applicant, values suitable to generate motor interferences, for a rotation, are preferably included in the ranges below:
angular velocity from 0.05 rad/s to 0.5 rad/s
acceleration from 0.01 rad/s² to 0.1 rad/s².

In general, the amplitude of these rotations is preferably from 3° to 30°.

For a movement, values suitable to generate motor interferences are preferably included in the following ranges:
speed from 0.02 m/s to 0.5 m/s
acceleration from 0.01 m/s² to 0.05 m/s².

The amplitude of the movement is instead preferably from 5 mm to 250 mm.

These rotations and these movements must be understood with respect to a reference position of the board, for example the undisturbed position. The rotation and movement values indicated above are therefore to be considered absolute values.

These values are however indicative. For some exercises, both for professional training and for rehabilitation, they could undergo variations as a function of the subject performing the exercise or of the result to be obtained.

These parameters can be set individually or in groups of one or more parameters. Preferably, the control unit 40 is configured to store some programs with which given values of the aforesaid parameters are associated.

For example, these programs can be indicated for different types of physical exercises or for different levels of difficulty or of intensity of the motor interferences generated.

For this purpose, the control unit is advantageously provided with an interface 41 that allows viewing of the aforesaid parameters and/or their modification by a user. Said interface 41 comprises, for example, a screen, a keypad or a touchscreen.

Besides the aforesaid parameters, the control unit 40 according to the invention can also allow programming of other parameters, such as the duration of the sequence of interferences, the time between one variation of position and the next (or frequency) and/or the total number of motor interferences (variations of position).

In a preferred variant, the control unit 40 is configured to program the sequence of motor interferences in conformity with a signal detected by sensor means 50, represented schematically in FIG. 1.

Said sensor means 50 can comprise, for example, one or more sensors capable of detecting one or more parameters that refer to the person performing the exercise and/or to the equipment used.

This allows the control unit 40 to receive said values measured and to modulate, also in real time, the intensity, the duration or the frequency of the motor interferences, as a function of the performance of the person performing the exercise.

Preferably said sensor means 50 can measure quantities, such as the position, the speed or the acceleration of at least a part of the body of the person performing the exercise and/or of a part of the equipment used.

For example, said sensor means 50 can detect the position of a dumbbell or a barbell held by the person, or the speed or the acceleration with which it is moved. Said sensor means can also detect the position, the speed or the acceleration of a movable part of a weight lifting machine or the speed of the belt of a treadmill positioned on the board 20. Said sensor means can also detect the position of the body of the person with respect to the supporting surface of the board 20.

According to the invention the sensor means 50 can comprise one or more of the following types of sensor:
optical sensors;
ultrasonic sensors;
inductive sensors;
video cameras;
accelerometers;
encoders;
magnetometers;
gyroscopes.

More in general, said sensor means can be contact sensors or contactless sensors.

These sensors can be mounted on the board 20, on the base 10 or on both. As a function of this arrangement, the positions, the speeds or the accelerations detected can be absolute or relative, with respect to a reference system integral with the board 20.

In some cases, said sensor means can also be applied to the body of the person performing the exercise.

According to the invention, the movable platform can comprise other sensor means 51 adapted to detect a force, or a weight force, applied to the board 20 or to a part of the equipment.

These sensor means 51 comprise, for example, load cells, or equivalent devices, installed on the board 20 and accessible from the upper surface 51.

Alternatively, or additionally, said sensor means 51 can be associated with the base 10 and/or with the actuator means 30.

According to the invention, the movable platform can be provided with further sensors to detect the energy expenditure of the person performing the exercise.

According to another aspect of the invention, the movable platform can comprise control means (not illustrated in the figure) connected to the control unit 40 and usable by a third person. Said third person can, for example, be a trainer in charge of monitoring the activity carried out by the person or by the people on the board 20.

According to the invention, said control means are configured to control one or more parameters of the sequence of motor interferences. In this case, some parameters of the sequence (for example the amplitude, the speed and the acceleration) can be preset in the control unit, while other parameters (the sense or the direction of the movements, their frequency and duration) can be imparted in real time by said third person with the control means.

Said control means can, for example, comprise one or more accelerometers applicable to the body of the third person. The movement of a part of the body, for example of a limb, can be interpreted by the control unit 40 as a command to impart to the board 20, a rotation about a given axis or a movement along a given direction.

Alternatively, or additionally, the control means can comprise a video camera adapted to film said third person. A recognition system, integrated in the control unit 40, is capable of detecting a given movement of the body of the third person and of generating a corresponding command for movement and/or rotation of the board 20.

According to another variant, the control means can comprise a voice control system that includes a microphone, usable by the third person, and a voice recognition system configured to associate a given word or phrase pronounced by the third person with a given command for movement or rotation of the board 20.

According to an aspect of the invention, the board 20 can be surrounded, at least in part, by guards 60, to prevent the person from accidentally falling from the board. Said guards 60 include, for example, rigid parapets, ropes, bands or the like.

FIGS. 2 to 8 illustrate some embodiments of the movable platform provided with different degrees of freedom and provided with different actuator means 30.

Figure 2:
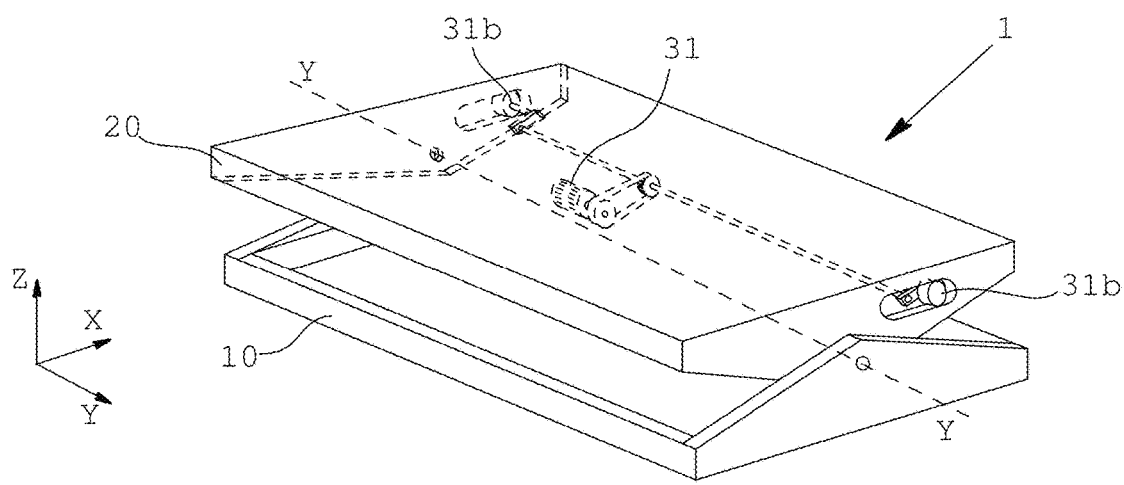
FIGS. 2 to 8 are perspective schematic views of the movable platform according to some embodiments of the invention.

FIG. 2 illustrates a movable platform in which the board 20 is connected to the base 10 so as to rotate about an axis Y substantially horizontal or substantially parallel to the surface on which the base 10 rests. Therefore, the board 20 only has one degree of freedom.

In this variant, the actuator means 30 can comprise a motor 31, preferably electric, connected directly to the board 20 or, as shown in the figure, by means of a cam system 31b.

This variant can be used, for example, to support a treadmill (not illustrated) in which the introduction of a degree of rotational freedom along the direction of movement of the belt is desired. This rotation is obtained by arranging the treadmill with the aforesaid direction of movement of the belt parallel to the rotation axis Y of the board 20.

In this variant the platform is provided with at least one sensor, optical or contact, operatively connected to the control unit, adapted to detect the rotation speed of the belt.

Figure 3:
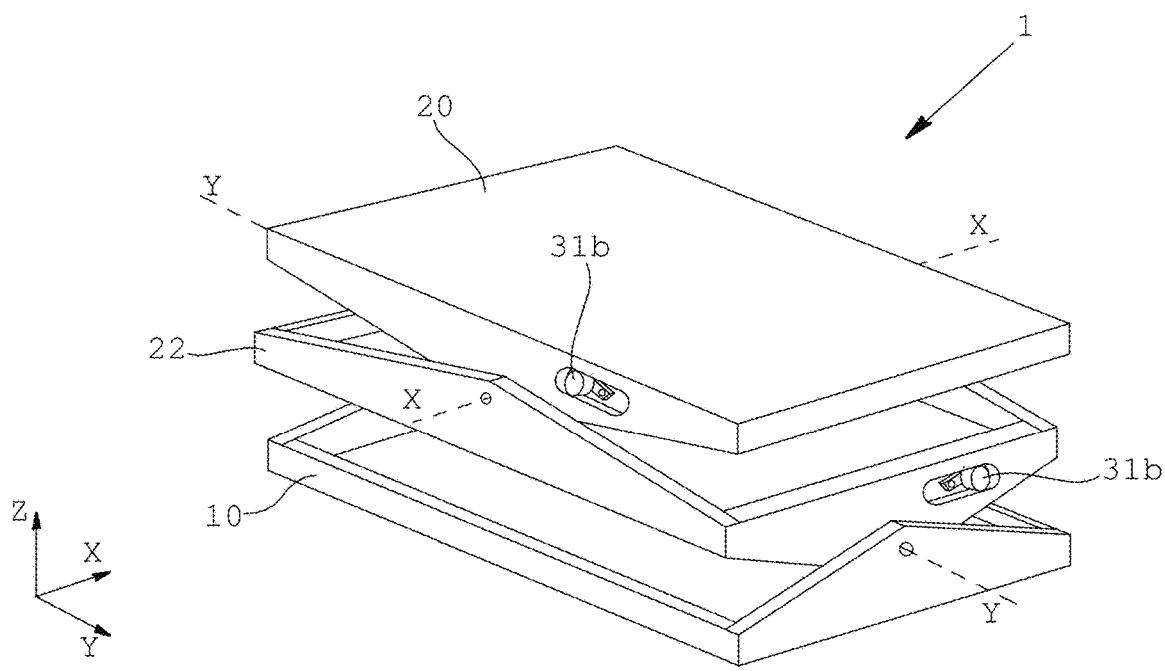

FIG. 3 illustrates another variant of the movable platform of FIG. 2.

In this variant, an intermediate joint 22 is interposed between the base 10 and the board 20. This intermediate joint 22 is hinged on the base 10 at a first axis X. The board 20 is in turn hinged on the intermediate joint 22 at a second axis Y.

Therefore, the board 20 has two degrees of freedom of rotation with respect to the two axes X, Y substantially perpendicular to each other.

The actuator means 30 can be the same illustrated for the variant of FIG. 2. This variant therefore includes at least two motors (not illustrated), each adapted to respectively move the intermediate joint 22 with respect to the base 10 and the board 20 with respect to the intermediate joint 22.

Figure 4:
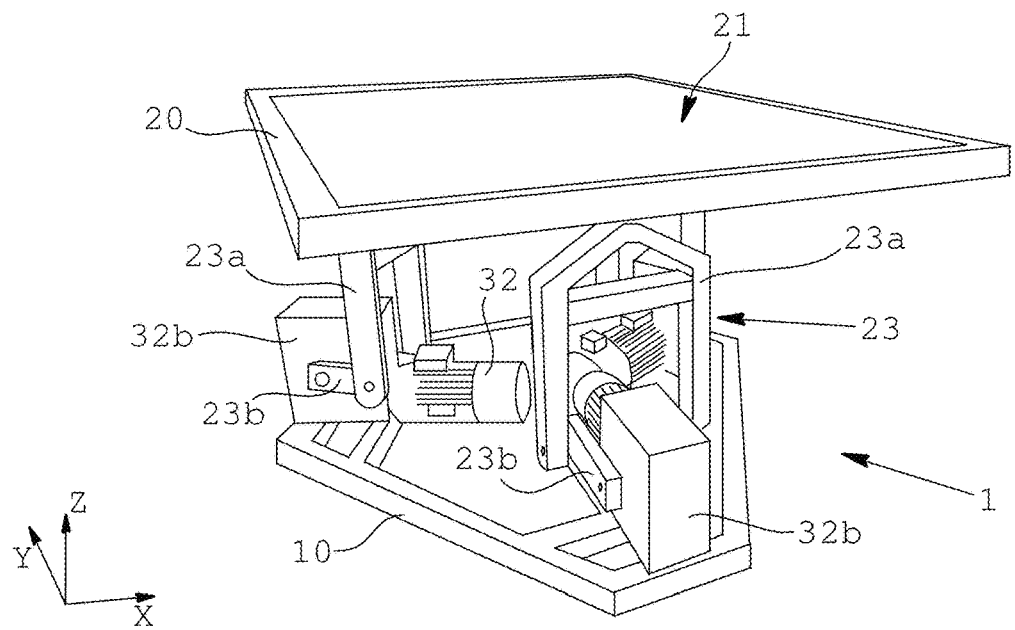

FIG. 4 illustrates a movable platform in which the board 20 is connected to the base 10 by means of at least three joints 23.

In the example, each joint 23 comprises a crank mechanism with a connecting rod 23a, connected to the lower side of the board 20; and a crank 23b, associated with the base 10 or with another part integral thereto. The connection between the connecting rods 23a and the board 20 is preferably made by means of ball joints (not illustrated). These connection points are positioned at the vertices of a triangle, preferably equilateral.

Each crank 23b is connected to a motor 32, preferably electric, by means of a gear motor 32b.

The combination of the rotation of the cranks 23b can generate rotations or translations of the board 20, or a combination thereof.

More in detail, when the cranks 23b are rotated simultaneously, the board 20 is moved rigidly along a substantially vertical axis Z, without varying its tilt.

Differently, by rotating the aforesaid cranks 23b in an unsynchronized manner, the board 20 is rotated with respect to the base, with one or two degrees of freedom, or optionally also translated simultaneously along the axis Z.

Figure 5:
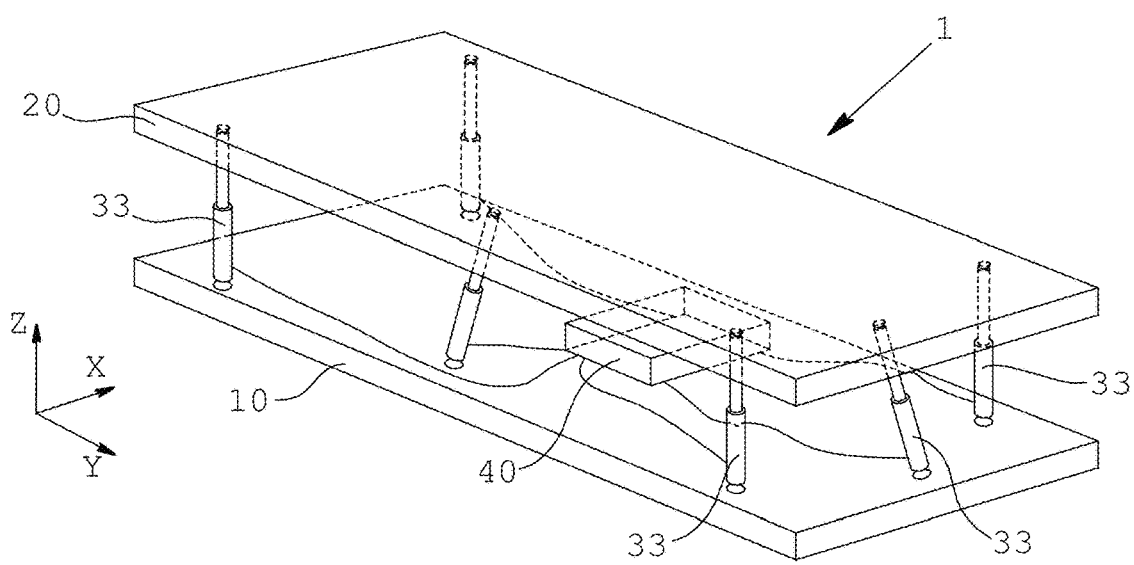

FIG. 5 illustrates a further variant of the movable platform, in which the board 20 is connected to the base 10 by means of a plurality of actuators 33.

Said actuators 33 are of linear type, preferably pneumatic, hydraulic or electric.

In this variant, at least three actuators 33 are provided to support the board 20 and give it three degrees of freedom of movement. To increase the stability of the board 20 and improve reactivity to the commands imparted by the control unit 40, at least four or at least six actuators 33 are provided.

Figure 6:
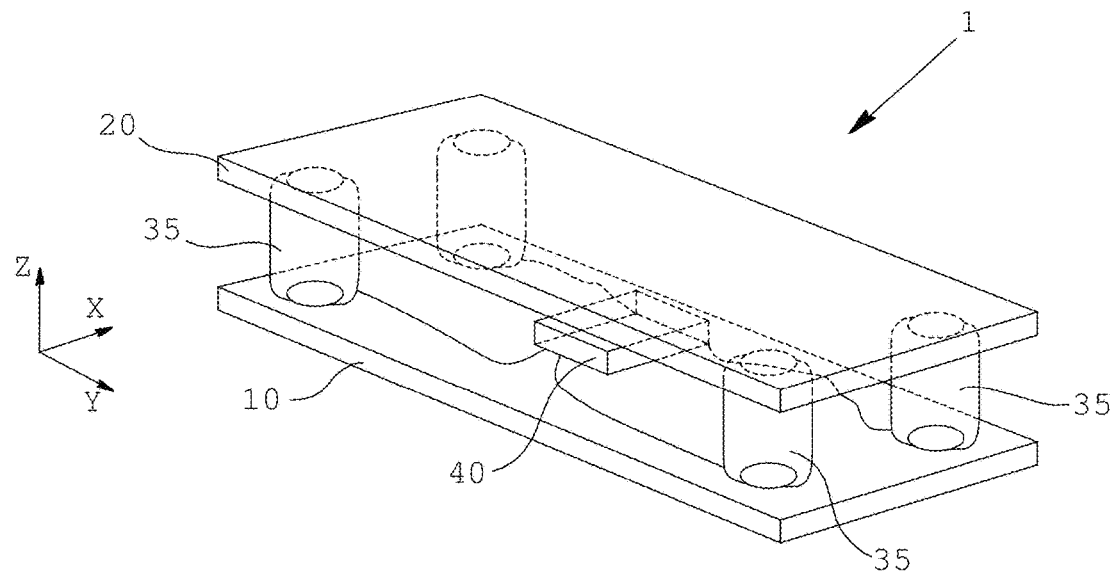

FIG. 6 illustrates a variant similar to that of FIG. 5. In this variant, the actuators 35 comprise pneumatic springs, or air springs, connected to a pump (not illustrated) controlled by the control unit 40.

Figure 7:
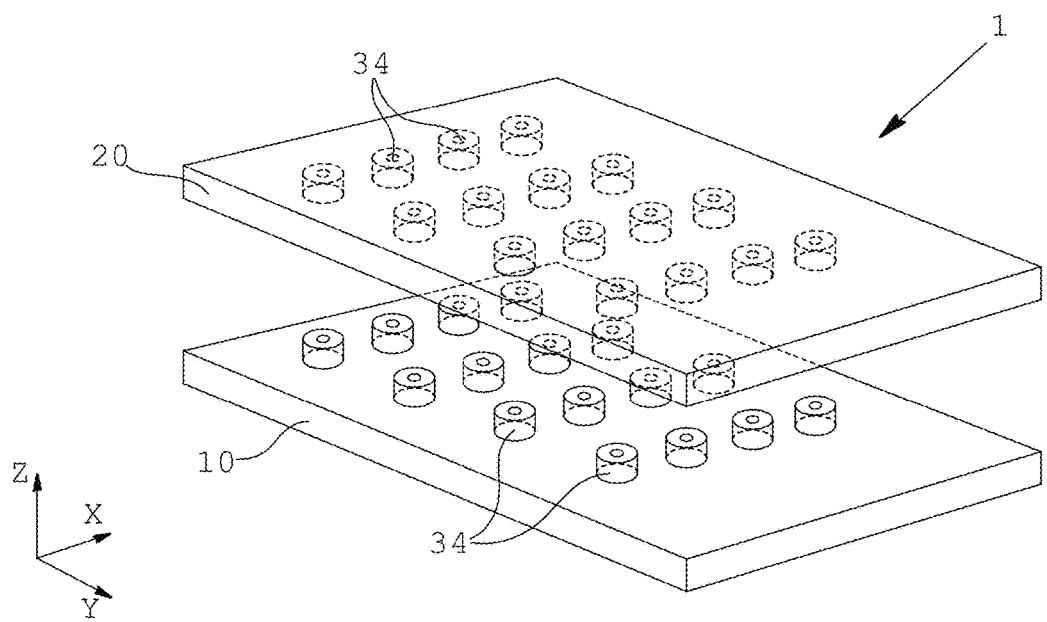

FIG. 7 illustrates a further variant of the movable platform, particularly suitable to generate motor interferences that simulate the unexpected loss of ground or yielding thereof.

This variant provides for the use of a plurality of pairs of electromagnets 34. The electromagnets 34 of a pair are arranged respectively on the base 10 and on the lower side of the board 20, and are oriented with opposite magnetic fields. Preferably said electromagnets 34 are distributed at least along the perimeter of the board 20.

The sum of the forces generated by the magnetic fields of the various pairs of electromagnets 34 maintains the board 20 suspended above the base 10.

The electromagnets 34 can be of the permanent magnet type with solenoid. In the absence of electric power, the opposite magnetic fields of the upper and lower permanent magnets repel the board 20 maintaining it at a distance from the base 10.

When said electromagnets are powered, this generates a magnetic field that, being equal and opposite to that of the permanent magnet, cancels the supporting effect.

By controlling some of all of said electromagnets 34 it is possible to tilt the board on one side or to move it vertically.

This last configuration allows the board 20 to reach accelerations comparable to those obtained by the unexpected loss of a point of support.

In another variant, the electromagnets 34 can be conventional electromagnets, in which the magnetic field is generated when they are powered by an electric current. This magnetic field is therefore canceled by interrupting the power supply.

Figure 8:
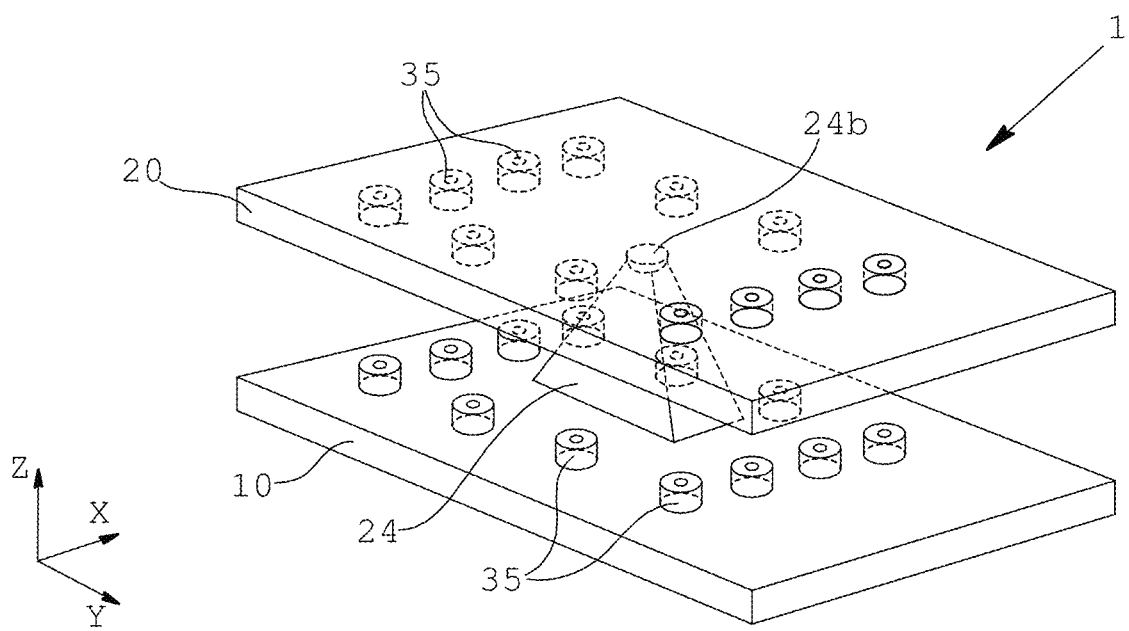

FIG. 8 illustrates a variant of the movable platform of FIG. 7. In this variant, the board 20 is also supported by a support 24 provided with a joint 24b at the top.

In this variant, the board 20 can therefore only rotate about the joint 24b under the action of the electromagnets 35.

In a further variant, not illustrated, the board is supported by a support provided with a joint such as that of the variant of FIG. 8. Said support is preferably connected at the centroid of the board.

In this variant the actuator means comprise two motors that move two crank mechanisms such as those of the variant of FIG. 4.

Preferably, the board is square or rectangular in shape. The connecting rods are connected to the board at two consecutive corners, preferably along the shorter side.

Figure 9:
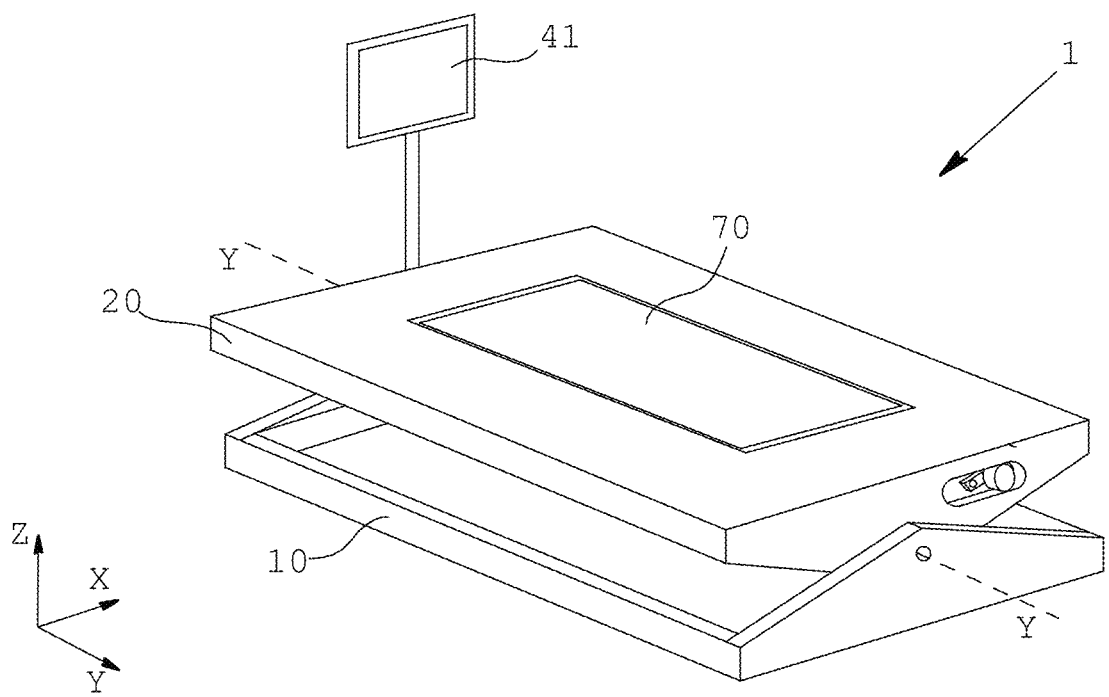
FIGS. 9 and 10 are respectively a perspective view and a side view of a variant of the movable platform in which sporting equipment is integrated.
Figure 10:
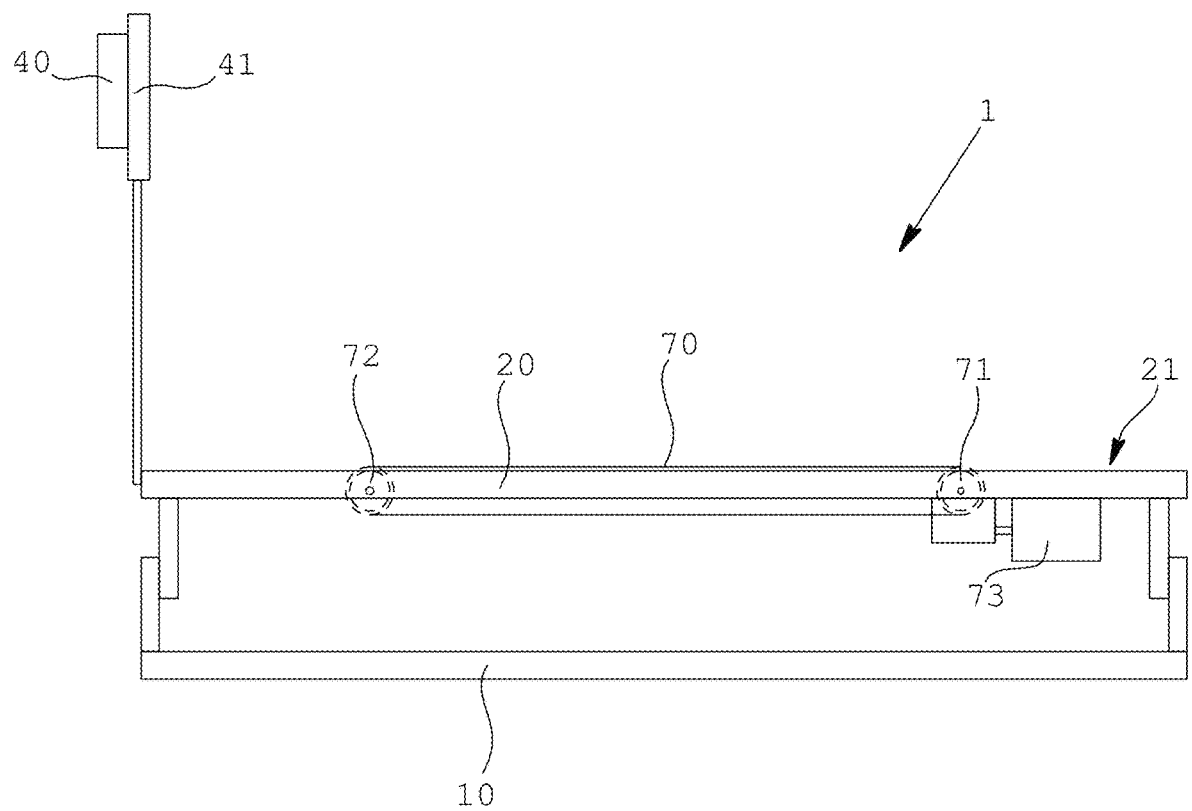

FIGS. 9 and 10 illustrate a further variant of the movable platform in which a treadmill is integrated.

In this variant, the board 20 is connected to the base 10 so as to rotate about at least one substantially horizontal axis Y. The board can therefore also have two or three degrees of freedom.

More in general, the board 20 can be moved with actuator means such as those described in the variants of FIGS. 2 to 8.

Hinged on the board 20 are two rollers 71, 72 arranged so that the respective rotation axes are parallel to each other and substantially parallel to the upper surface 21 of the board. In practice, the axes of the rollers 71, 72 lie in a plane substantially parallel to the upper surface 21.

Wound about the rollers 71, 72 is a belt 70 that has at least an upper branch positioned above said upper surface 21 of the board so that a person on the board can stand on it. A motor 73 is connected to at least one of said rollers 71, 72 to rotate said belt 70 and allow the person to walk or run on the board 20. The motor 73 is connected to the control unit 40 and managed thereby. For example, by means of the interface 41 of the control unit 40, it is possible to program both the speed of rotation of the belt 70 and the sequence of motor interferences generated by the rotations of the board 20 about the axis Y.

Also in this variant, the movable platform can be provided with one or more sensors operatively associated with the control unit 40 by means of the which said control unit 40 can vary in real time the parameters of the sequence of motor interferences.

The invention has been described for illustrative and non-limiting purposes according to some preferred embodiments thereof. Those skilled in the art may find numerous other embodiments and variants, all falling within the scope of protection of the claims below.

BIBLIOGRAPHY

Shumway-Cook A & Woollacott M H. Motor control: Theory and Practical Applications (2nd ed). Philadelphia. Lippincott Williams & Wilkins, 2001.

Nasher L M. Sensory, neuromuscular and biomechanical contribution to human balance. In Pw. Duncan Ed, Balance: Proceedings of the APTA forum. Virginia: American Physical Therapy, 1990.

Mcllroy W E, Maki B. Age-related changes in compensatory stepping in response to unpredictable perturbations. J of Gerontology, 1996, 51A: 289-296.

Shumway-Cook A & Woollacott M. Attentional demands and postural control: the effects of sensory context. J of Gerontology, 2000, 55A:M10-16.

Shumway-Cook A & Horak F B. Assessing the influence of sensory interaction on balance. Physical Therapy. 1986, 66(10):1548-1550.

The invention claimed is:

1. A movable platform for physical exercise comprising:
    a fixed base (10);
    at least one board (20) having an upper surface (21) that can accommodate at least one person who must perform a physical exercise or also sporting equipment, said board (20) being connected to said base (20) and rotatable about at least one axis (X, Y) and/or movable at least along one direction (Z);
    actuator means (30) interposed between the base (10) and the board (20), the actuator means (30) configured to impart to the board (20) at least a rotation about said at least one axis (X, Y), at least a movement at least along said direction (Z), or combinations of these movements;
    a control unit (40) operatively connected to the actuator means (30), the control unit (40) configured to control activation or deactivation of said actuator means (30) to rotate and/or move the board (20) between a reference position and perturbed positions, said control unit (40) generating a sequence of motor interferences that influence the balance of the person performing the exercise; and
    sensor means (50, 51), operatively connected to the control unit (40), the sensor means (50, 51) configured to measure at least one parameter selected from a position, a speed, and an acceleration of one or more parts of the body of the person performing the exercise or the sporting equipment or both the person performing the exercise and the sporting equipment,
    wherein said sensor means (50, 51) are selected from:
        accelerometers or gyroscopes applied to the body of the person or to the sporting equipment,
        optical sensors, ultrasonic sensors, inductive sensors or encoders mounted on the sporting equipment, and video cameras, and
    wherein said control unit (40) is configured to program said sequence of motor interferences as a function of said at least one parameter detected, for determining a type of movement to impart to the board, an initial moment, a rapidity of said movement, and a duration or an intensity of said movement.

2. The movable platform (1) according to claim 1, wherein said sensor means (51) are further configured to measure energy expenditure of the person.

3. The movable platform (1) according to claim 1, wherein said parameter is a force or weight force applied to the board or to a part of the equipment.

4. The movable platform (1) according to claim 1, wherein the control unit (40) is configured to correct the parameters of a sequence of motor interferences being performed, as a function of the parameters detected by the sensor means (50, 51).

5. The movable platform (1) according to claim 1, further comprising an interface (41), operatively connected to the control unit (40), configured to allow viewing of information concerning the sequence of motor interferences and to program the parameters of said sequence.

6. The movable platform (1) according to claim 1, wherein sequences of motor interferences having given parameters are stored in the control unit (40).

7. The movable platform (1) according to claim 1, further comprising control means connected to the control unit (40) and configured to impart one or more parameters of the sequence of motor interferences, said control means being usable by a third person.

8. The movable platform (1) according to claim 7, wherein said control means comprise one or more of the following components:
    one or more accelerometers wearable by said third person;
    a voice control system managed by said third person; and
    one or more video cameras to film said third person.

9. The movable platform (1) according to claim 1, wherein said actuator means (30) are configured to impart to the board (20) a rotation about at least one axis with:
    an angle from 3° to 30°;
    and/or a movement along at least one direction with:
    an amplitude from 5 mm to 250 mm.

10. The movable platform (1) according to claim 1, wherein said actuator means (30) are configured to impart to the board (20) a rotation about at least one axis with:
    an angular velocity from 0.05 rad/s to 0.5 rad/s;
    an acceleration from 0.01 rad/s$^2$ to 0.1 rad/s$^2$ and/or a movement along at least one direction with:
    a speed from 0.02 m/s to 0.5 m/s; and
    an acceleration from 0.01 m/s$^2$ to 0.05 m/s$^2$.

11. The movable platform (1) according to claim 1, wherein said control unit (40) is configured to control the duration, the intensity and/or the frequency of the movements of the board (20) that generate the sequence of motor interferences.

12. The movable platform (1) according to claim 1, wherein said actuator means (30) comprise pneumatic actuators (3) selected from pneumatic cylinders or air springs.

13. The movable platform (1) according to claim 1, wherein said actuator means (1) comprise electromagnets (34, 35).

14. The movable platform (1) according to claim 1, wherein the board (20) is supported by the base through joints (23, 24) or directly through said actuators (33, 34, 35).

15. The movable platform (1) according to claim 1, further comprising:
    a pair of rollers (71, 72) rotatingly connected to the board (20) and arranged so that the respective rotation axes are parallel to one another and substantially parallel to the upper surface (21) of the board (20);

a belt (70), wound around said rollers and arranged so as to have at least an upper branch positioned above said upper surface (21) of the board (20); and at least one motor (73) connected to at least one of said rollers to rotate said belt (70).

16. The movable platform (1) according to claim 1, wherein said sensor means (51) are further configured to measure a heart rate of the person.

17. The movable platform (1) according to claim 1, wherein said sensor means (50, 51) comprise accelerometers or gyroscopes applied to the body of the person or to the sporting equipment.

18. The movable platform (1) according to claim 1, wherein said sensor means (50, 51) comprise optical sensors, ultrasonic sensors, inductive sensors or encoders mounted on the sporting equipment.

19. The movable platform (1) according to claim 1, wherein said sensor means (50, 51) comprise video cameras.

20. The movable platform (1) according to claim 1, wherein, said board (20) is rotatable about the at least one axis (X, Y) and movable at least along the one direction (Z), the actuator means (30) is configured to impart to the board (20) both the at least a rotation about said at least one axis (X, Y) and the at least a movement at least along said direction (Z), and the control unit (40) is configured to control the activation and the deactivation of said actuator means (30) to angularly rotate and linearly move the board (20) between the reference position and the perturbed positions, said control unit (40) being configured to program said sequence of motor interferences as the function of said at least one parameter detected, for determining the type of movement to impart to the board, the initial moment, the rapidity of said movement, and the duration or the intensity of said movement.

* * * * *